United States Patent
Sandwith (10) Patent No.: US 10,835,411 B2
(45) Date of Patent: Nov. 17, 2020

(54) ANATOMICALLY NEUTRAL ARM SUPPORT APPARATUS

(71) Applicant: Belle Sandwith, Loyalton, CA (US)

(72) Inventor: Belle Sandwith, Loyalton, CA (US)

(*) Notice: Subject to any disclaimer, the term of this patent is extended or adjusted under 35 U.S.C. 154(b) by 383 days.

(21) Appl. No.: 15/408,520

(22) Filed: Jan. 18, 2017

(65) Prior Publication Data

US 2017/0202696 A1 Jul. 20, 2017

Related U.S. Application Data (60) Provisional application No. 62/280,059, filed on Jan. 18, 2016.

(51) Int. Cl.
*A61F 5/37* (2006.01)
*A61F 7/10* (2006.01)
*A61F 7/02* (2006.01)

(52) U.S. Cl.
CPC ............ *A61F 5/3746* (2013.01); *A61F 5/373* (2013.01); *A61F 7/10* (2013.01); *A61F 2007/023* (2013.01); *A61F 2007/0238* (2013.01); *A61F 2007/108* (2013.01)

(58) Field of Classification Search
CPC ...... A61F 5/0118; A61F 5/05858; A61F 5/37; A61F 5/3715; A61F 5/3723; A61F 5/373; A61F 5/3738; A61F 5/3746; A61F 5/3753; A61F 2007/023; A61F 2007/0238; A61F 2007/108; A61F 5/0102; A61F 5/0104; A61F 5/013; A61F 5/026; A61F 5/028; A61F 5/04; A61F 5/058; A61F 5/05808; A61F 5/05841; A61F 5/05866; A61F 5/40; A61F 13/104; A61F 13/107; A41D 15/00; A41D 27/10; B65G 7/12; A47D 13/02
USPC .... 602/4; 128/872, 873, 874, 875, 876, 881, 128/878; 224/157–158, 160
See application file for complete search history.

(56) References Cited

U.S. PATENT DOCUMENTS

| | | | |
|---|---|---|---|
| 2,012,848 A | 9/1934 | Fruhauf | |
| 2,344,844 A | 9/1934 | Ross | |
| 2,560,243 A * | 7/1951 | Peterson | A61F 5/3746 602/4 |
| 3,559,640 A | 2/1971 | Beckett | |
| 4,601,285 A | 7/1986 | Whitchurch | |
| 5,095,894 A * | 3/1992 | Marble | A61F 5/3746 128/878 |

(Continued)

*Primary Examiner* — Rachael E Bredefeld
*Assistant Examiner* — Caitlin A Carreiro
(74) *Attorney, Agent, or Firm* — Richard Batt (57) ABSTRACT

A medical apparatus for supporting the shoulder complex and humerus in a neutral position includes an upper body garment and a forearm sleeve adjustably fastened to the garment in an anterior and transverse orientation. The patient inserts her arm in the sleeve and fastens an elbow strap around the elbow to secure the forearm in a horizontal anterior position near waistline. The sleeve is adjustable in position to place the humerus inline with the spinal column, thereby preventing adduction and internal rotation of the glenohumeral joint. A weight distribution strap further elevates the sleeve and forearm. The strap is secured in a superior anterior region of the shoulder and spaced from the neck thereby preventing injury to the internal anatomies in the neck region. Optionally, thermal therapy to the shoulder is supported by a removable thermal therapy pouch.

20 Claims, 7 Drawing Sheets

(56) References Cited

U.S. PATENT DOCUMENTS

| | | | |
|---|---|---|---|
| 5,144,694 A * | 9/1992 | Conrad Da oud | A63B 21/065 |
| | | | 2/102 |
| 5,358,470 A * | 10/1994 | Johnson | A61F 5/3746 |
| | | | 128/DIG. 15 |
| 5,848,956 A | 12/1998 | Grettner | |
| 6,102,877 A | 8/2000 | Joslin | |
| 6,404,449 B1 | 6/2002 | Moore | |
| 6,453,904 B1 | 9/2002 | Wilson | |
| 6,595,936 B1 * | 7/2003 | Oladipo | A61F 5/3746 |
| | | | 602/20 |
| 6,770,044 B1 | 8/2004 | Joslin | |
| 6,974,429 B2 * | 12/2005 | Moore | A41D 13/1245 |
| | | | 128/878 |
| 7,037,281 B1 | 5/2006 | Neil | |
| 8,196,588 B1 * | 6/2012 | Krenzel | A61F 5/3738 |
| | | | 128/869 |
| 8,733,365 B2 | 5/2014 | Krenzel | |
| 2003/0187373 A1 * | 10/2003 | Gaylord | A61F 5/3738 |
| | | | 602/4 |
| 2007/0043311 A1 * | 2/2007 | Jaggan-Vince | A61F 5/3746 |
| | | | 602/4 |
| 2008/0119770 A1 * | 5/2008 | Miller | A61F 5/3738 |
| | | | 602/4 |
| 2010/0064411 A1 | 3/2010 | Price | |
| 2012/0143109 A1 | 6/2012 | Krenzel | |
| 2013/0110027 A1 | 5/2013 | Kobler | |
| 2013/0317401 A1 | 11/2013 | Joslin | |
| 2015/0190270 A1 * | 7/2015 | Boone | A61F 5/3738 |
| | | | 602/4 |
| 2016/0278963 A1 * | 9/2016 | Webster | A61F 5/026 |

\* cited by examiner

ANATOMICALLY NEUTRAL ARM SUPPORT APPARATUS

CROSS-REFERENCE TO RELATED APPLICATIONS

This application claims priority to and the benefit of Provisional Application No. 62/280,059, filed Jan. 18, 2016, and entitled "ANATOMICALLY NEUTRAL ARM SUPPORT APPARATUS."

BACKGROUND OF THE INVENTION

The shoulder joint is a complex system that includes a ball and socket-type joint formed of the humerus and scapula. The scapula forms a shallow pocket surrounded by muscles, tendons and connective tissue that support the humerus. Ordinarily, the humerus is suspended from the joint in an anatomically neutral position where the scapula is centered in its plane of motion and the humerus is inline (namely, parallel) with the spine, free of rotational forces.

The shoulder joint works in conjunction with the Cervical/Thoracic spine, ribs and torso due to the numerous shoulder muscle attachments about the upper body. This anatomy is also referred to as the Shoulder Girdle Complex. Due to the above described complexity, the shoulder joint is the most mobile multidirectional joint in the body. However, it is also the least stable complex. Consequently, when the shoulder joint is injured, its great mobility and minimal stability make the shoulder joint difficult to properly treat.

Unfortunately, injuries to the shoulder are not uncommon. When conservative care treatment does not suffice, shoulder injuries are treated with surgery. Recovery from the shoulder surgery is challenging because of the complex anatomy of the shoulder.

Following a shoulder injury or surgery, the patient is typically required to wear a sling to limit movement on the shoulder joint. Unfortunately, a conventional sling does not hold the arm in an anatomically neutral state. Additionally, conventional slings do not supply a means for applying thermal therapy.

Various conventional slings attempt to solve some of the above challenges in caring for shoulder injuries. For example, a conventional arm sling 10 (see, e.g., the Ultimate Arm Sling®, manufactured by Joslin Orthopedic Gear, Brisbane, Calif.) depicted in FIGS. 1-2. The sling 10 suspends the distal end of the humerus (or elbow) and forearm. A single strap 12 runs from the medial end of the sling 14 over the opposing shoulder to the lateral end of the sling 16. The sling shown in FIGS. 1-2 urges the entire shoulder complex of the humerus, scapula and glenohumeral joint into an undesirable non-anatomically neutral position during recovery. The humerus and glenohumeral joint are pulled into flexion, internal rotation (R) and horizontal adduction (A). Indeed, the humerus forms an angle (theta) with the neutral spine equal to or greater than 45 degrees. The scapula is pulled into protraction. The entire shoulder girdle complex is pulled anteriorly, compromising the integrity of neutral spinal alignment, resulting in a slouching/kyphotic posture. This effect is uncomfortable, undesirable, and exacerbated in females and overweight individuals.

Figure 1:
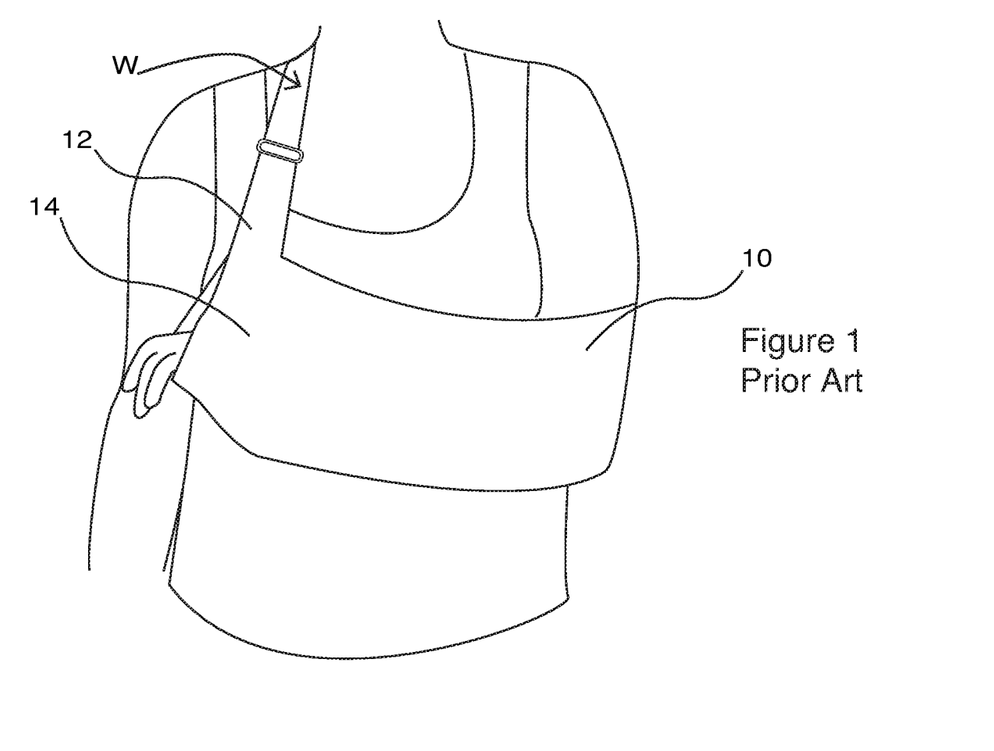
FIG. 1 is a front view of a prior art sling supporting the left arm of a patient.
Figure 2:
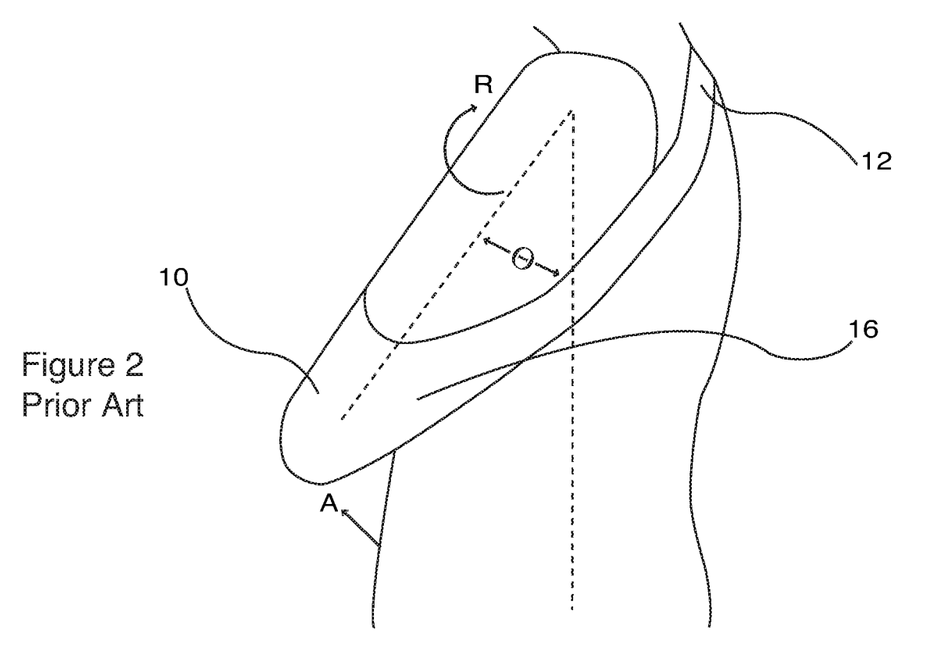
FIG. 2 is a side view of the prior art sling shown in FIG. 1.

Additionally, the singular strap 12 across the shoulder focuses the entire weight (W) of the arm onto the upper trapezius muscle and the brachial plexus often causing neurapraxia and/or scoliotic changes to the spine. This is painful and undesirable.

Additionally, the sling 10 does not limit lateral movement of the arm in the sense that the arm may rock like a pendulum. The arm, when placed in the sling, is bent. The weight of the arm is unevenly distributed, creating an off balance and pendulum effect. Gravity pulls on the hand causing the sling to rotationally slip across several planes. Constant repositioning is required to correct for the rotational slippage of the sling. This is undesirable and hinders recovery.

Sling 10 and other designs have attempted to eliminate slippage by running the strap from the forearm pouch completely around the torso, and attaching the strap to the ends of the pouch with an array of clips. The attachment, however, is complicated and inconvenient.

Additionally, slings require a base garment to be worn underneath the sling. After an injury and surgery, it is very difficult to put on a shirt, much more to put on a cumbersome sling with straps and clips. The slings cannot be worn without a base garment because the sling frequently slips and repositions itself, causing skin chaffing.

Others have attempted to overcome some of the above mentioned shortcomings. Descriptions of various slings, vests, and other arm supports can be found in U.S. Pat. Nos. 2,012,848; 2,344,844; 3,559,640; 4,601,285; 5,095,894; 5,792,083; 6,102,877; 6,406,449; 6,453,904; 6,595,936; 6,974,429; 6,770,044; 8,196,588; 8,733,365 and U.S. Patent Publication No. 2013/0317401.

However, the previous slings, vests, and arm supports do not overcome the above mentioned shortcomings. In addition to failing to overcome some of the above described shortcomings, some of the previous sling designs are specific to the left and right side. Some have prepositioned snaps, clasps, magnets or buttons which prevent size and position adjustment.

Accordingly, there is still a need for an improved apparatus to support the shoulder complex and humerus in a neutral position, to be freely and conveniently adjustable, non-size or side specific, evenly distribute the weight of the arm, and wearable as an undergarment or over garment as desired and the need for an easily applicable thermal therapy modality.

SUMMARY OF THE INVENTION

A medical apparatus for supporting the shoulder complex and humerus in a neutral position and distributing the weight of the supported arm about the shoulder girdle includes an upper body garment, a forearm sleeve adjustably fastened to the subclavicular region of the upper body garment, and an elongate elbow strap fastenable to the sleeve.

In embodiments, the upper body garment has an anterior portion, a posterior portion, a left shoulder portion and right shoulder portion, and an aperture for the neck between the left shoulder portion and the right shoulder portion. The garment may have a vest type shape and be made of soft dynamic material such as a hook and loop compatible fabric.

In embodiments, the forearm sleeve has a medial opening, a lateral opening, and a pocket extending therebetween to accommodate the forearm. In embodiments the forearm sleeve is attached to the garment high on the torso via a transverse attachment region on the rear surface of the sleeve. Preferably, the sleeve is attached just inferior to the clavicle and lateral of the midline.

In embodiments, the forearm sleeve has a trapezoid shape. In embodiments, the sides of the trapezoid are equal such that the sleeve is usable on either the left or right side.

In embodiments, the elongate elbow strap has a first end, second end, and elongate body therebetween. The first end and second end are removably mountable to the lateral opening of the forearm sleeve. The combination of the trapezoid pocket and the elbow stabilization strap serve to securely hold the arm, preventing lateral/posterior/rotational movement.

In embodiments, a weight distribution strap attaches to the garment at one or more superiorly disposed attachments points, and does not span, contact or loop around the neck. In embodiments, the weight distribution strap is adjustable and allows the patient to adjust the tension as needed as she changes position such as, for example, from sitting to standing, or from standing to laying herself in bed.

The medical apparatus holds the arm and shoulder complex in a comfortable anatomically neutral position conducive to healing.

In embodiments the garment includes a semi-tailored fit of dynamic (e.g., elastic) fabric that distributes the weight of the injured arm to the shoulder girdle and across the entire torso. This serves to eliminate neurapraxia and scoliotic problems associated with conventional or prior art devices, described above.

In embodiments, the medical apparatus fits the upper body or torso and includes an openable seam or zipper so that it may be conveniently worn over clothing.

Additional advantages of various embodiments of the present invention include wearing the medical arm support apparatus itself as a garment. This is very useful in the acute recovery phase following surgery or injury. Wearing the medical apparatus itself as a garment is especially helpful for women who do not have the option of wearing a sling without a shirt because putting on a shirt may be too painful to do after surgery or an injury.

In embodiments, a medical apparatus, assembly, or system to support the forearm, and secure the shoulder complex and humerus in a neutral position comprises any one or more of the structures described herein.

In embodiments, a therapeutic method to facilitate recovery following shoulder surgery comprises supporting the forearm in a horizontal orientation; and securing the shoulder complex and the humerus in a neutral position wherein the supporting and securing are performed by any one or more of the steps or instructions described herein. In embodiments, the method includes the step of delivering a thermal therapy to shoulder. The thermal therapy may be delivered as described herein.

A medical kit to support the arm of an individual following shoulder injury or surgery comprises an apparatus as described herein; and a set of instructions to wear the apparatus and to fasten a forearm pocket to an anterior region of the garment, inferior of a clavicle of the individual, and lateral of midline such that the humerus and shoulder complex are secured in an anatomically neutral position.

An advantage of embodiments of the invention is to immobilize the arm in all planes in a neutral position via the transverse forearm sleeve and the elbow stabilization strap. The transverse forearm sleeve also reduces gravitational pressure on the glenohumeral joint enhancing recovery.

The description, objects and advantages of the present invention will become apparent from the detailed description to follow, together with the accompanying drawings.

DETAILED DESCRIPTION OF THE INVENTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Unless the context dictates otherwise, reference to "she" includes "he" and visa versa. Reference to "patient" includes the user, client, injured individual, or another individual intended to wear the apparatus described herein.

Reference to a singular item includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Figure 3:
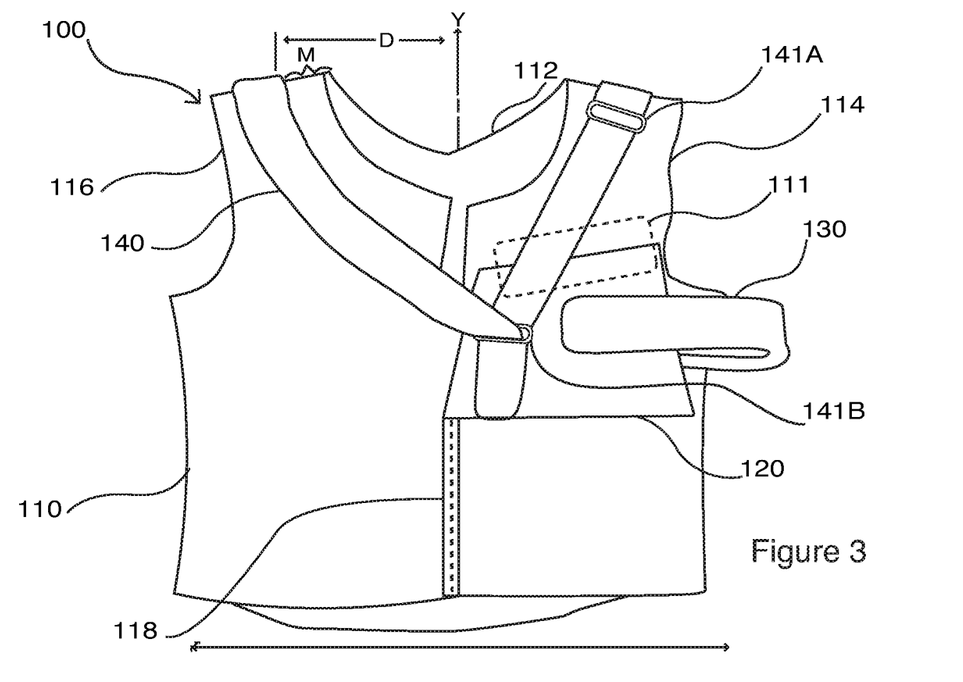
FIG. 3 is a front view of an arm support vest in accordance with one embodiment of the present invention.

FIG. 3 is a front view of an arm support apparatus 100. The arm support apparatus 100 is shown having an upper body garment 110 and a forearm sleeve 120 secured on the anterior side or front portion of the upper body garment.

In embodiments, the sleeve 120 is attached to upper body garment in a sleeve attachment zone or region 111 which preferably is located in the vicinity just inferior of the clavicle, and lateral of the midline (Y).

A weight distribution strap 140 further supports the arm. As described herein, the components of the apparatus operate together to distribute the weight of the arm away from the patient's neck, and to hold the shoulder complex and humerus in a body natural or neutral state. Adjustment may be made to the arm support 100 to modify position, tension, elevation so as to place the humerus inline with the spine, and to eliminate internal rotation and horizontal adduction on the glenohumeral joint.

The garment 110 is preferably sized to snugly fit on the upper torso of a patient. The garment includes an aperture or opening 112 for the neck, and two openings 114, 116 for the arms. The garment shown in FIGS. 3-4 has a vest-like shape. The apertures may have a circular, oval or v-neck shape.

An openable seam 118 is shown serving to facilitate taking the garment on and off. In embodiments, the seam is closable with a zipper. However, the invention is not so limited and other means for closing the seam include without limitation buttons, snaps, hook and loop fasteners, or another suitable means to close the seam.

The arm support may be made from a variety of materials. Exemplary materials for the garment include fabrics made of cotton, nylon, and polyesters. In an embodiment, the anterior or front portion of the garment is made of nylon fabric under the trade name Veltex® brand and suitable for use with hook fasteners such as Velcro® Brand Hook fasteners.

Figure 4:
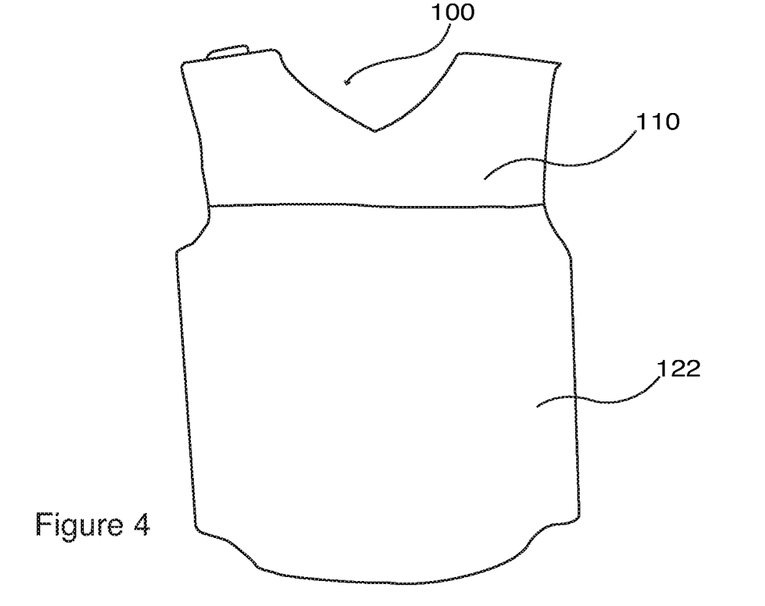
FIG. 4 is a rear view of the arm support vest shown in FIG. 3.

FIG. 4 shows a posterior or rear view of the garment 100 and includes an elastic rear section 122. The rear section shown in FIG. 4 is made of a different material than the front section of the garment. The rear section may be adapted to flex or stretch, serving to distribute the weight of the arm to a larger area of the torso. Exemplary materials for the rear section may include elastic fabrics such as, without limitation, nylon/polyester blends, Spandex®, cotton/polyester blends.

As described herein, an elongate elbow strap 130 may be adjustably fastened to the forearm sleeve and around the elbow (or distal end of the humerus) to secure the arm therein.

The arm support apparatus shown in FIG. 3 also includes a weight distribution strap 140 to elevate the forearm sleeve, and to distribute the weight of the arm across both sides of the body, and garment 110. To this end, the weight distribution strap 140 is preferably attached to each shoulder portion of the garment 110. The strap 140 is shown not extending around the neck. Additionally, the strap 140 rests at posteriorly disposed attachment points midway between the neck opening 112 and each of the arm openings 114, 116. The sufficient margin (M) prevents the weight of the arm and associated strap from impinging on the vasculature, and nerves in the neck area, and prevents serious conditions such as neurapraxia. In embodiments, the strap is spaced ($D_1$) from the midline of neck where $D_1$ ranges from 10 to 15 cm. In embodiments (M) may range from 2 to 6 cm.

Weight distribution strap 140 is shown having buckles 141A, 141B for adjusting the length of the strap from the shoulder attachment points to the sleeve. Adjusting the length of the strap serves to redistribute the weight on the shoulders arising from supporting the arm.

Figure 5A:
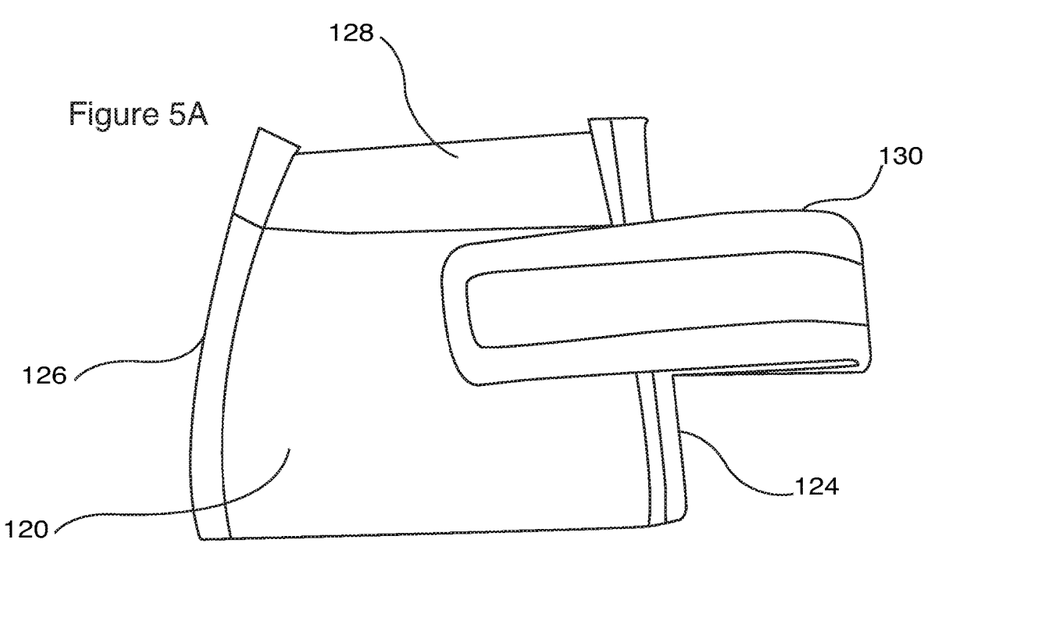
FIG. 5a is a front view of a forearm sleeve and an elbow strap.
Figure 5B:
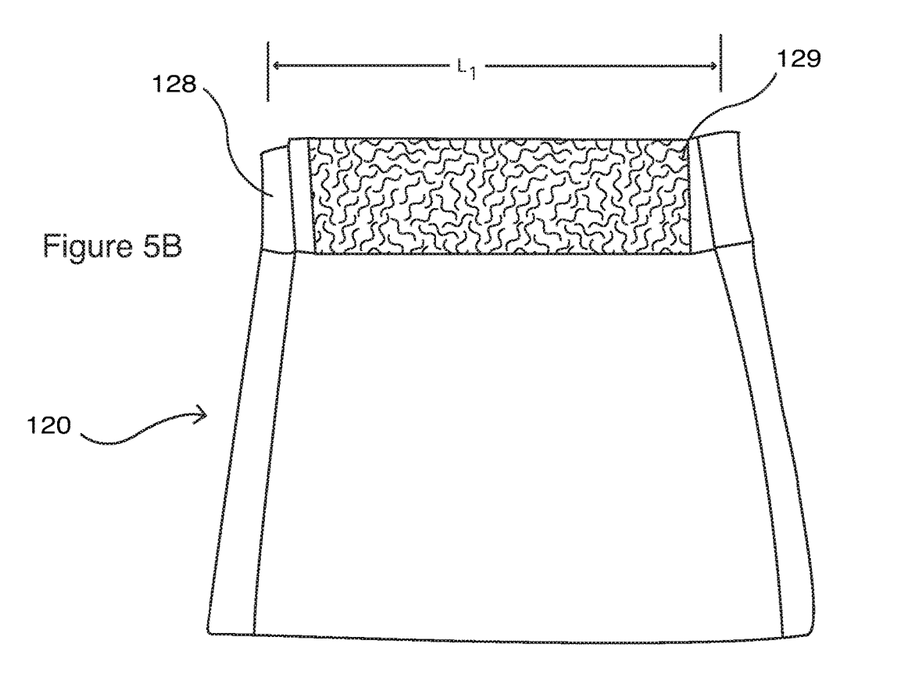
FIG. 5b is a rear view of a forearm sleeve.

FIG. 5a and FIG. 5b are front and rear views, respectively, of the forearm sleeve 120. FIG. 5a additionally shows elbow strap 130 fastened thereto. The sleeve 120 has a lateral opening 124, medial opening 126, and lumen or pocket extending therethrough for receiving the forearm of the patient. The lumen preferably is sized and adapted to surround the forearm. For example, the lumen may have a tubular or cylindrical interior.

With reference to FIG. 5b, sleeve preferably (but not necessarily) has a trapezoidal shape. Exemplary dimensions include L1 and L2 where L1 ranges from 12 to 22 cm and L2 ranges from 22-32 cm such that a ratio (R) may be defined equal to L1:L2 in the range from 1 to 3 and preferably is about 1.5-2. The sleeve height may range from 14 to 22 cm, and preferably about 18-20 cm.

The sleeve may be formed of the same materials as the garment. Upper transverse panel 128 preferably includes a strip 129 of hook fastener on the rearward side to adjustably mount the sleeve on the garment 110.

Figure 6:
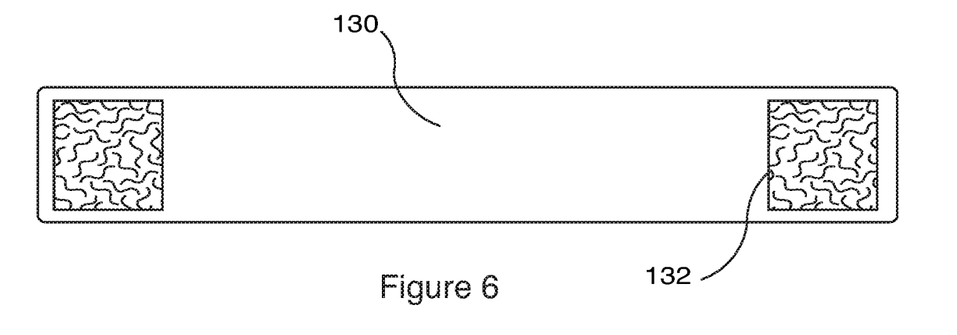
FIG. 6 is a rear view of an elbow strap in an unfolded state.

FIG. 6 shows elbow strap 130 in an unfolded position. At least one strip of hook fastener 132 is provided to secure the strap to the sleeve, and to adjust the position of the strap relative to the sleeve to form a snug and secure fit with the arm.

Figure 7:
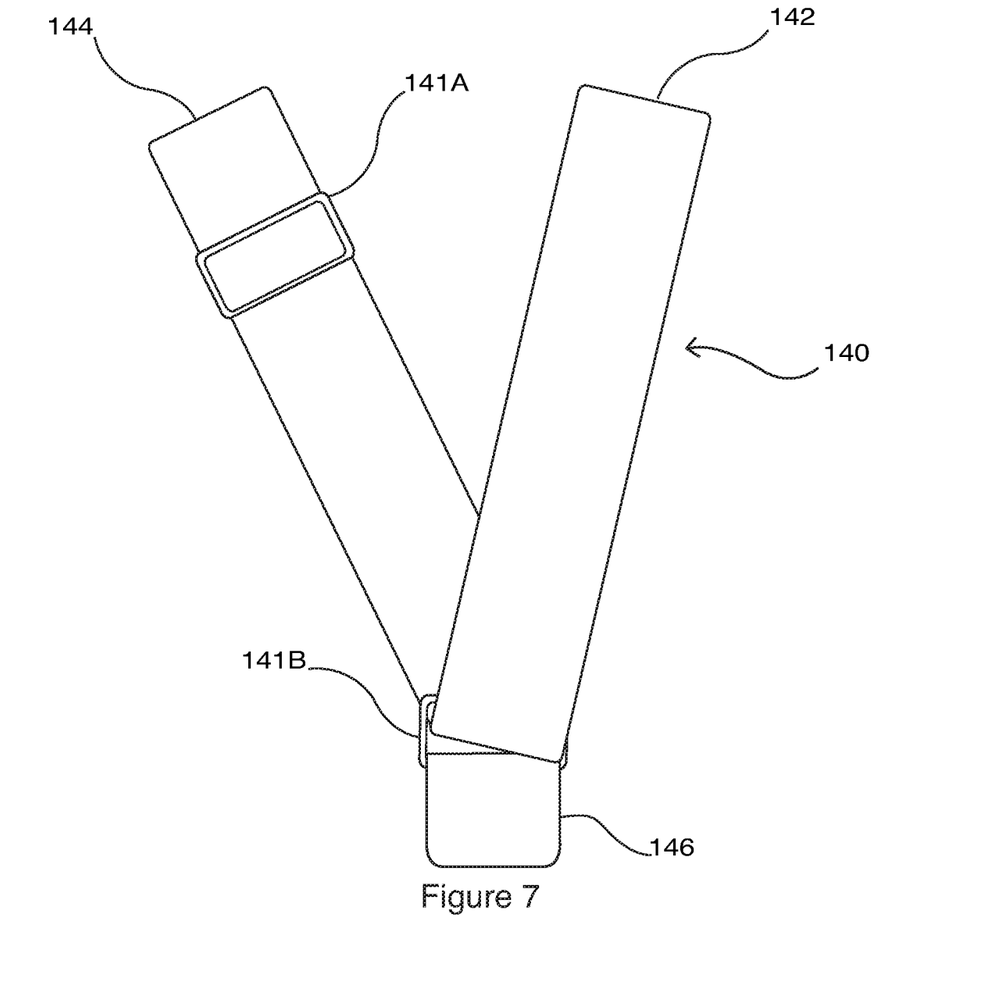
FIG. 7 is front view of a weight distribution strap.

FIG. 7 shows a front view of the weight distribution strap with the garment and sleeve removed for clarity. The strap 140 is shown having a first attachment area 142, second attachment area 144, and sleeve attachment area 146 for fastening to the garment's left shoulder, right shoulder, and forearm sleeve respectively. The strap 140 may be fastened by hook and fasteners to the applicable portions of the garment. Additionally, a plurality of buckles 141A, 141B (e.g., without limitation, Tri-Glide Brand® buckles) are shown for adjusting the tightness, elevation, or otherwise adjust the position of the arm. The strap may be made of various materials including without limitation static materials, nylon webbing, cotton webbing or polyester.

Figure 8:
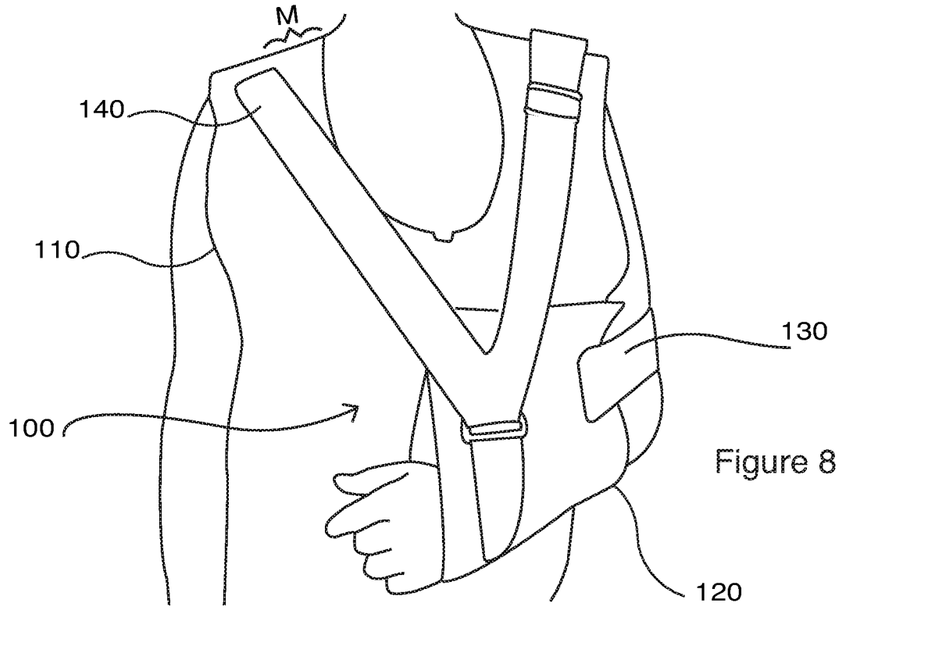
FIG. 8 is an illustration of the arm support vest shown in FIG. 3 supporting the left arm of a patient, and showing a distal end of the forearm of the individual not extending beyond the midline.
Figure 9:
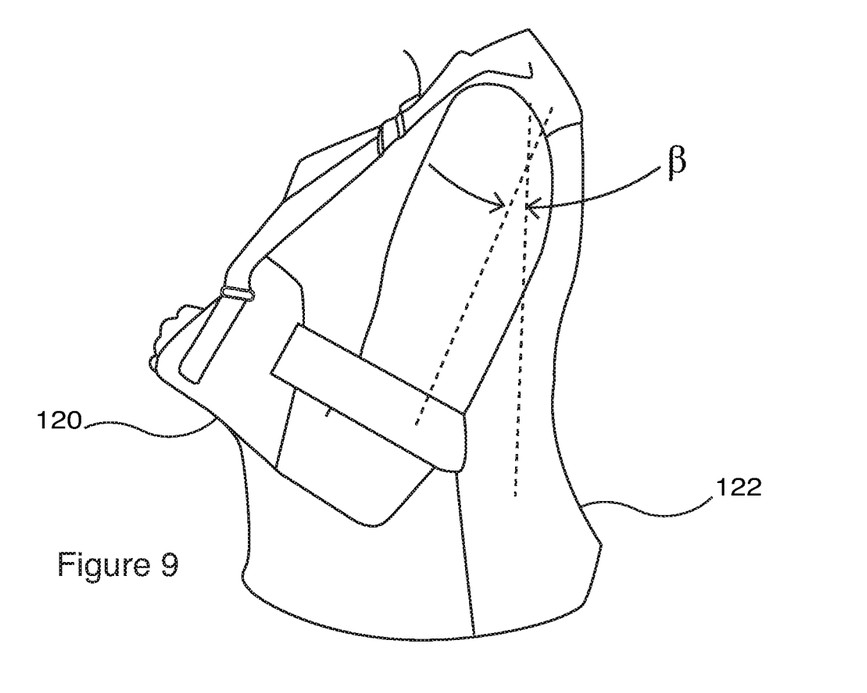
FIG. 9 is a side view of the arm support vest and patient shown in FIG. 8.

FIGS. 8 and 9 show the arm support 100 holding an arm of a patient in a humerus neutral position. As shown, a vest-shaped upper torso garment 110 is snugly fit to the patient. Sleeve 120 is secured to the garment front portion in a horizontal arrangement using Velcro® hook and loop fasteners. Elbow strap is fastened to the lateral end of the sleeve and secures the elbow to the sleeve. Weight distribution strap is attached to the right shoulder and left shoulder of the garment, and to the sleeve. The attachment points of the weight distribution strap are spaced from the neck to distribute the weight of the shoulder away from the neck, and to more evenly distribute the weight across the entire upper torso. As discussed above, an elastic rear panel 122 having greater elasticity than the front portion, may be incorporated into the design to more evenly distribute the weight of the arm across the entire upper torso of the patient.

Adjustment may be made to the arm support to modify position, tension, elevation to place the humerus inline with the spine, to eliminate internal rotation and horizontal adduction on the glenohumeral joint. For example, attachment of the various components may be performed using hook and loop fasteners, magnets, buttons, snaps, zippers, or other types of fasteners. In embodiments, stitches and adhesives may also be employed to connect or join components.

In embodiments, the arm support apparatus is constructed such that an angle (beta) between the humerus and the spine is less than or equal to 30 degrees, and more preferably less than or equal to 25 degrees. In preferred embodiments, the device is constructed so as to place the angle (β) at an angle less than or equal to 20 degrees. Consequently, the shoulder complex and humerus are held in an anatomically neutral orientation.

Additionally, as shown the first and second attachment portions of the weight distribution strap 140 is off the neck, and off the back. A margin (M) or space from the neck is shown which serves to protect the neck from the injuries described above.

Figures 10, 11:
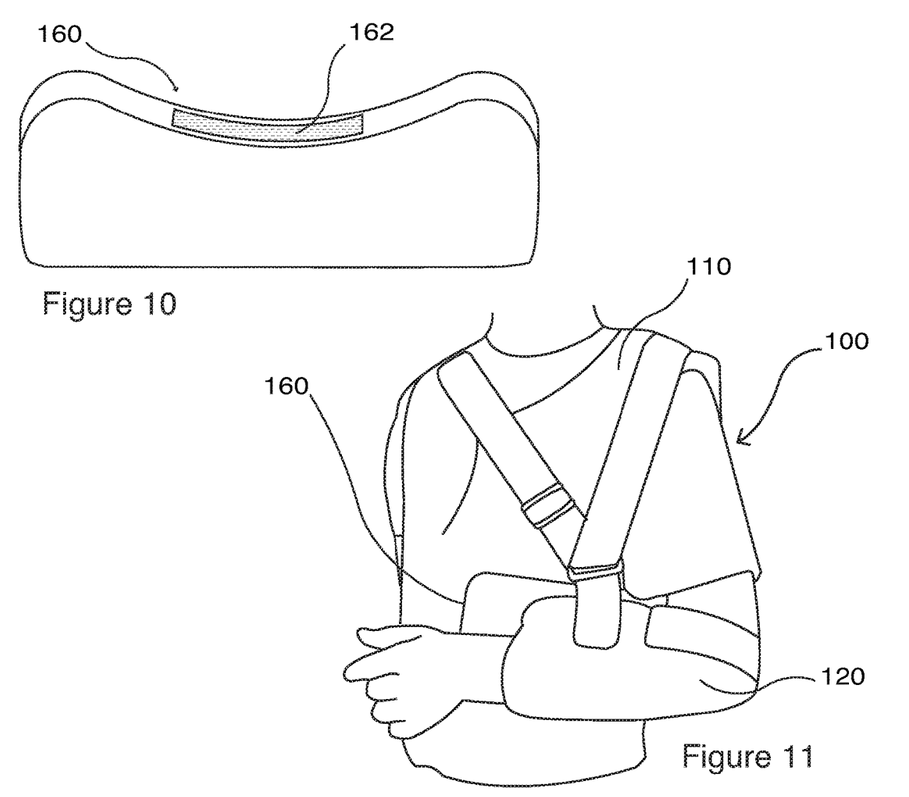
FIG. 10 is a rear view of a pillow.
FIG. 11. is an illustration of the arm support vest and pillow shown in FIG. 3 and FIG. 10, respectively, supporting the left arm of a patient.
Figure 12:
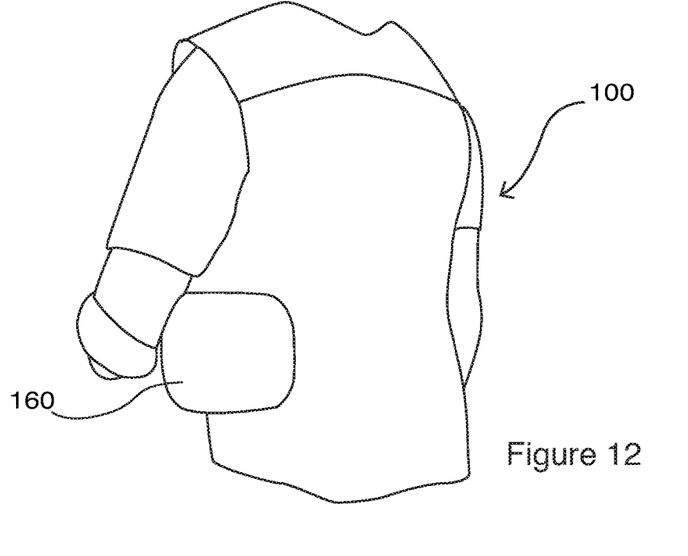
FIG. 12 is a rearward side view of the arm support vest, pillow, and patient shown in FIG. 11.

FIG. 10 shows a shaped "abduction" pillow or spacer 160 to position the forearm anterior to the waist of the patient. Pillow may further serve to reduce the rotation and adduction on the glenohumeral joint. The spacer 160 is shown having a concave rear surface to receive the waist or profile of the patient. The spacer may be comprised of a foam core, and include a cover or fabric outer surface. Hook fasteners may be provided on the rear side of the spacer to conveniently attach the pillow to the vest. Pillow may also include buckles to receive various straps of the apparatus.

Figure 13:
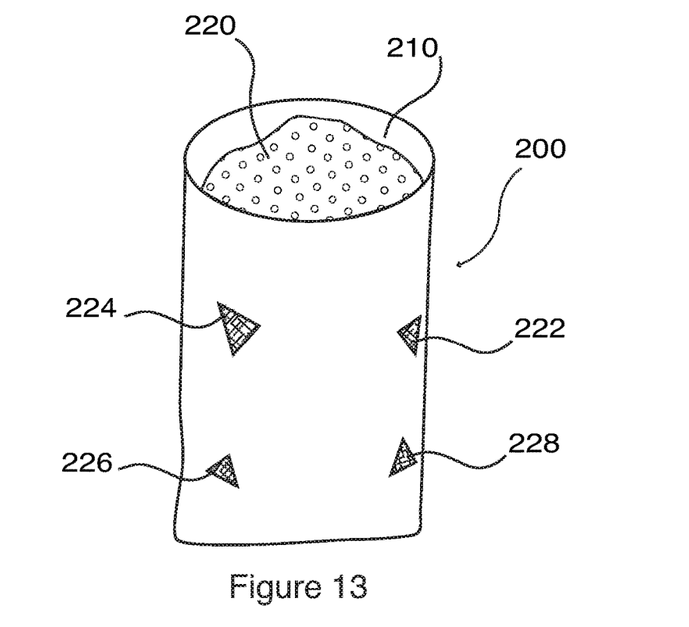
FIG. 13. is a top view of a thermal therapy sack.

FIG. 13. is a top view of an ice sack 200 for delivering a thermal therapy to the tissue. Ordinarily, desirable thermal therapy modalities are challenging to apply due to the above described anatomy, required shoulder motion, and other above mentioned complexities. Examples of thermal therapies include cryotherapy and heat. Cryotherapy involves the use of ice or a cold pack placed in thermal contact with the tissue to reduce pain and inflammation, and to speed healing. Heat therapy is another recommended for chronic degenerative conditions.

FIG. 13 shows thermal therapy pouch 200 including a cavity 210 for receiving ice, ice bag 220, a cold pack or heat packs. Fasteners 222, 224, 226, 228 are located along the superior side of the sack for engaging the support vest as described herein. Examples of fasteners include hook loop type such as Velcro®, or other means to removably attach, and in some embodiments, permanently attach the pouch to the body garment.

Optionally, but not necessarily, the sack 200 may be closeable with closing means including fasteners, pins, zippers, buttons and other fastening means.

Exemplary materials for the sack include materials described herein, or in some embodiments, designated regions of thermal insulating materials to reduce heat loss. In embodiments, the sack applies directional thermal activity, and has regions of efficient heat transfer, and other regions of heat insulation. In embodiments, the sack or pouch has a face and back, wherein the face is made of a material that efficiently transfers thermal energy, and the back is made of a material that prohibits transfer for thermal energy. Example materials for the back include thermal insulating materials including thermal batting such as, for example, Insul-Bright and Insul-Shine both offered by The Warm Company (Lynwood, Wash.). Additionally, the sides and top of the pouch 200 may also be made of the heat insulating materials.

Figure 14:
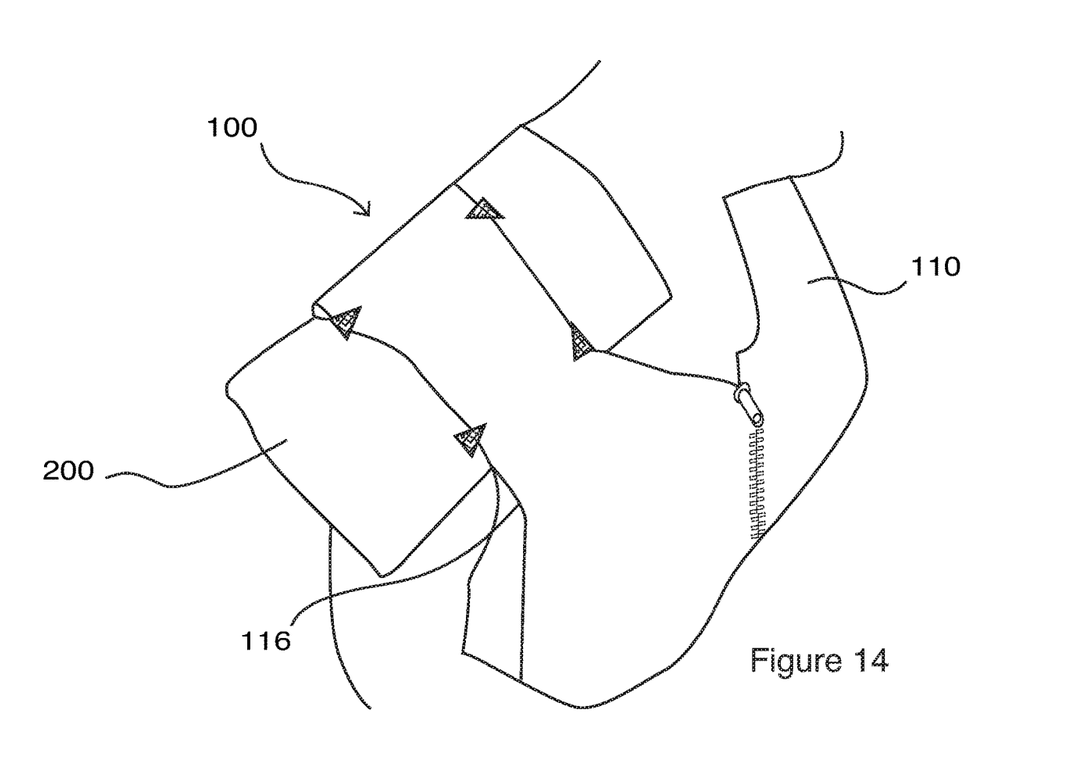
FIG. 14 is an illustration of an arm support vest and the thermal therapy sack shown in FIG. 13 supporting the right arm of a patient.

FIG. 14 is an illustration of an arm support vest 100 and the thermal pouch 200 shown in FIG. 13 engaged to the vest. In particular, FIG. 14 shows thermal pouch 200 disposed within opening 116 of the vest 100. Fasteners 222-228 are engaged to the shoulder portion of the garment 110. The thermal pouch 200 supports a thermal therapy modality to the shoulder complex. In embodiments, the detachable thermal therapy pouch 200 holds the desired therapeutic modality in place, and encases the main components of the shoulder girdle.

The thermal pouch and garment combination shown in FIG. 14 thus provide desirable arm support, and thermal therapy.

Many modifications and variations of the present invention are possible in light of the above teachings. It is therefore to be understood that within the scope of the appended claims the invention may be practiced otherwise than as specifically described.

We claim:

1. A medical apparatus for supporting an arm of an individual, said individual having a spine, neck, shoulder complex, shoulder girdle, humerus, and forearm, and a midline, and configured for securing the shoulder complex and humerus in an anatomically neutral position, the apparatus comprising:
an upper body garment comprising a front portion, a rear portion, a left shoulder portion, a right shoulder portion, and an opening for the neck;
a forearm sleeve comprising a medial opening, a lateral opening, and a pocket therebetween to accommodate the forearm,
a weight distribution strap comprising a first end removably fastened to the upper body garment at a first attachment point on the left shoulder portion and a second end removably fastened to the upper body garment at a second attachment point on the right shoulder portion and such that the weight distribution strap does not extend around the individual, and said weight distribution strap further being removably fastened to the forearm sleeve by a sleeve attachment area configured for attachment to an outer surface of the forearm sleeve; wherein the sleeve attachment area is coupled to the weight distribution strap by a first buckle positioned intermediate the first end and the second end of the weight distribution strap and extends therefrom such that the first and second ends of the weight distribution strap and the sleeve attachment area are arranged in a Y-shaped configuration; and further comprising a second buckle provided on the weight distribution strap and configured for adjusting an elevation of the forearm sleeve; wherein a rear surface of the forearm sleeve is adjustably mountable to the front portion of the upper body garment in a horizontal arrangement, inferior to a clavicle of the individual, and lateral of the midline of the individual and is configured such that a distal end of the forearm of the individual does not extend beyond said midline; and
an elongate elbow strap comprising a first end, second end, and a body therebetween, the first end and second end being removably mountable to the forearm sleeve, and across the lateral opening of the forearm sleeve;
wherein the upper body garment, forearm sleeve, weight distribution strap, and elongate elbow strap are configured to cooperate to secure the shoulder complex and the humerus in the anatomically neutral position defined by maintaining (a) the forearm of the individual lateral of the midline and (b) an angle between the humerus and the midline at less than or equal to 30 degrees when viewed laterally, and are configured for distributing weight of the forearm about the shoulder girdle of the individual.

2. The apparatus of claim 1 wherein the upper body garment has a vest shape.

3. The apparatus of claim 2 wherein the upper body garment further comprises an openable seam extending vertically along the front portion.

4. The apparatus of claim 3 wherein the seam comprises a zipper.

5. The apparatus of claim 1 wherein the second end of the weight distribution strap is configured to be attached to the right shoulder portion intermediate of the neck and the right shoulder of the individual, thereby defining a margin between the neck, and the second attachment point, and serving to distribute the weight of the supported arm away from the neck.

6. The apparatus of claim 5 wherein the second attachment point is configured to be at least 10 cm from the midline of the individual, and superiorly disposed.

7. The apparatus of claim 6 wherein the weight distribution strap is fastened to the right shoulder portion using hook and loop fasteners.

8. The apparatus of claim 1 wherein the rear portion is formed of material comprising a higher elasticity than the front portion.

9. The apparatus of claim 8 wherein the rear portion is formed of a material selected from cotton/poly blends, an elastic synthetic fiber or fabric made from a polymer containing polyurethane, and nylon/poly blends.

10. The apparatus of claim 1 wherein the front portion comprises a fabric that is compatible with hook fasteners.

11. The apparatus of claim 1 wherein the forearm sleeve has a trapezoidal shape.

12. The apparatus of claim 1 wherein the forearm sleeve comprises a discrete posterior transverse panel of hook and loop fastener.

13. The apparatus of claim 1 further comprising a soft spacer between the forearm sleeve and the upper body garment.

14. The apparatus of claim 1 wherein the upper body garment, forearm sleeve, weight distribution strap, and elongate elbow strap are configured to maintain the angle between the humerus and the midline at less than or equal to 20 degrees.

15. The apparatus of claim 1 further comprising a detachable thermal therapy pouch, and wherein the pouch or the upper body garment comprises at least one fastener to secure the pouch to one of the left shoulder portion and right shoulder portion of the upper body garment.

16. A medical apparatus for supporting a forearm and securing a shoulder complex and humerus of a patient, said patient having a right shoulder, a spine and a midline, said medical apparatus comprising:
an upper body garment comprising a front portion, a rear portion, a left shoulder portion and right shoulder portion, and an opening for a neck of the patient between the left shoulder portion and the right shoulder portion;
a forearm sleeve comprising a medial opening, a lateral opening, and a pocket therebetween to accommodate the forearm;
an elongate elbow strap comprising a first end, second end, and body therebetween, the first end and second end being removably mountable to the forearm sleeve; and
a weight distribution strap comprising a first end being removably fastened to the left shoulder portion at a first attachment point, and a second end being removably fastened to the right shoulder portion at a second attachment point;
a sleeve attachment area coupled to the weight distribution strap by a first buckle positioned intermediate the first end and the second end of the weight distribution strap and extending therefrom such that the first and second ends of the weight distribution strap and the sleeve attachment area are arranged in a Y-shaped configuration, wherein the sleeve attachment area is configured for being removably fastened to an outer surface of the forearm sleeve, wherein each of the first attachment point and second attachment point is superiorly disposed on the upper body garment, and further comprising a second buckle provided on the weight distribution strap and configured for adjusting an elevation of the forearm sleeve along the front portion of the upper body garment; and
wherein the upper body garment, forearm sleeve, weight distribution strap, and elongate elbow strap are configured to cooperate to secure the shoulder complex and the humerus in an anatomically neutral position defined by maintaining (a) the forearm of the patient lateral of the midline, and (b) an angle between the humerus and a vertical axis extending through the spine when viewed laterally at less than or equal to 30 degrees.

17. The apparatus of claim 16 wherein the weight distribution strap is fastened to the upper body garment such that the weight distribution strap avoids extending or looping around the patient.

18. The apparatus of claim 17 wherein the second attachment point is configured to be intermediate of the neck and the right shoulder, thereby defining a margin between the neck and the second attachment point, and serving to distribute weight of a supported arm away from the neck.

19. The apparatus of claim 18 wherein the upper body garment, forearm sleeve, weight distribution strap, and elongate elbow strap are adapted to maintain the angle between the humerus and the vertical axis at less than or equal to 20 degrees.

20. The apparatus of claim 16 further comprising a detachable thermal therapy pouch, wherein the pouch or the upper body garment comprises at least one fastener to secure the pouch to one of the left shoulder portion and right shoulder portion of the upper body garment.

* * * * *